(12) United States Patent
Nishino et al.

(10) Patent No.: US 8,053,738 B2
(45) Date of Patent: Nov. 8, 2011

(54) RADIOGRAPHIC IMAGE DETECTION DEVICE AND RADIOGRAPHIC IMAGE DETECTION SYSTEM

(75) Inventors: Naoyuki Nishino, Kanagawa (JP); Yutaka Yoshida, Kanagawa (JP); Yasunori Ohta, Kanagawa (JP); Keiji Tsubota, Kanagawa (JP); Takeshi Kamiya, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 6 days.

(21) Appl. No.: 12/547,506

(22) Filed: Aug. 26, 2009

(65) Prior Publication Data
US 2010/0054399 A1  Mar. 4, 2010

(30) Foreign Application Priority Data

Aug. 28, 2008  (JP) ................................. 2008-219300
Aug. 13, 2009  (JP) ................................. 2009-187840

(51) Int. Cl.
*H01L 27/146*  (2006.01)

(52) U.S. Cl. .......... 250/370.09; 250/370.08; 250/370.01

(58) Field of Classification Search ............. 250/370.09, 250/580–589, 370.01, 370.08
See application file for complete search history.

(56) References Cited

U.S. PATENT DOCUMENTS

| 7,396,158 | B2 | 7/2008 | Grosse | |
| 2006/0113481 | A1* | 6/2006 | Murphy et al. | 250/370.09 |
| 2006/0256928 | A1* | 11/2006 | Grosse | 378/189 |
| 2008/0240358 | A1* | 10/2008 | Utschig et al. | 378/107 |

FOREIGN PATENT DOCUMENTS

JP  2008-145101 A  6/2008

* cited by examiner

*Primary Examiner* — David Porta
*Assistant Examiner* — Christine Sung
(74) *Attorney, Agent, or Firm* — SOLARIS Intellectual Property Group, PLLC

(57) ABSTRACT

A radiographic image detection device includes a radiation detector and a handle portion. The radiation detector detects radiation that has passed through a subject and has been irradiated thereon, and outputs image information expressing a radiographic image corresponding to a detected radiation amount. The handle portion is provided at a side surface of the radiation detector and configured to be grasped, and has a notification section that gives notice of an operating state of the radiation detector.

6 Claims, 16 Drawing Sheets

RADIOGRAPHIC IMAGE DETECTION DEVICE AND RADIOGRAPHIC IMAGE DETECTION SYSTEM

CROSS-REFERENCE TO RELATED APPLICATION

This application claims priority under 35 USC 119 from Japanese Patent Applications No. 2008-219300 filed on Aug. 28, 2008, and No. 2009-187840 filed on Aug. 13, 2009, the disclosures of which are incorporated by reference herein.

BACKGROUND OF THE INVENTION

1. Field of the Invention

The present invention relates to a radiographic image detection device and a radiographic image detection system, and in particular, to a portable radiographic image detection device and a radiographic image detection system.

2. Description of the Related Art

Flat Panel Detectors (FPDs), in which an X-ray-sensitive layer is disposed on a Thin Film Transistor (TFT) active matrix substrate and that can convert X-rays directly into digital data, have been put into practice in recent years. Portable radiographic image detection devices (hereinafter also called "electronic cassettes"), that generate image data expressing a radiographic image manifested by radiation irradiated and transmitted through a subject by using an FPD or the like and that store the generated image data, have been put into practice. In a radiographic image detection system using such an electronic cassette, the electronic cassette and a radiation generator, that generates radiation such as X-rays, are disposed with a space therebetween. At the time of capturing (shooting) a radiographic image, the subject is positioned between the radiation generator and the electronic cassette. In a case in which the image capture state is upright positioning, the electronic cassette is mounted to an uprighting stand. In a case in which the image capture state is laying positioning, the electronic cassette is inserted between a bed and the subject.

Due to the electronic cassette being portable, the electronic cassette is handled at places that are away from a console that is for setting the image capture conditions at the electronic cassette and for confirming the image that is based on the image data generated at the electronic cassette. Thus, there has been proposed an electronic cassette at which, in order to confirm operation of the electronic cassette, an indicator, that displays and gives notice of the charged state of a rechargeable battery and the operation state and the like, is provided at the casing of the electronic cassette such that the operator can visually confirm the charged state and the like of the electronic cassette (see, for example, Japanese Patent Application Laid-Open (JP-A) No. 2008-145101).

However, with the electronic cassette of JP-A No. 2008-145101, in cases in which the electronic cassette is disposed between the subject and an uprighting stand or a bed, there are cases in which the indicator is covered by the subject, depending on the orientation of the electronic cassette or other factors. In such cases, there may be cases in which the operating state of the electronic cassette cannot be confirmed.

SUMMARY OF THE INVENTION

In view of the aforementioned, the present invention provides a radiographic image detection device and a radiographic image detection system at which confirmation of the operating state can be carried out easily.

An aspect of the present invention is a radiographic image detection device including: a radiation detector that detects radiation that has passed through a subject and has been irradiated thereon, and outputs image information expressing a radiographic image corresponding to a detected radiation amount; and a handle portion provided at a side surface of the radiation detector and configured to be grasped, and having a notification section that gives notice of an operating state of the radiation detector.

BRIEF DESCRIPTION OF THE DRAWINGS

Exemplary embodiments of the present invention will be described in detail based on the following figures, wherein.

DETAILED DESCRIPTION OF THE INVENTION

Figure 1A:
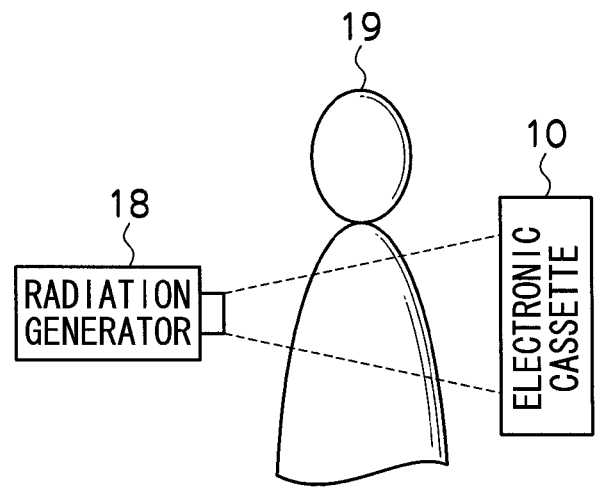
FIG. 1A is a schematic diagram showing the placement of an electronic cassette of the exemplary embodiments at the time of capturing a radiographic image.

As shown in FIG. 1A, a portable radiographic image detection device (hereinafter referred to as "electronic cassette") 10 according to the first exemplary embodiment is disposed a distance away from a radiation generator 18 that generates radiation such as X rays during capturing of a radiographic image. In this positional relationship, the space between the radiation generator 18 and the electronic cassette 10 is an image capture position for a subject 19 to be disposed. When image capture of a radiographic image is instructed, the radiation generator 18 emits radiation of a radiation amount that corresponds to an image capture condition given beforehand. The radiation emitted from the radiation generator 18 carries image information as a result of transmitting through the subject 19 positioned in the image capture position, and is thereafter irradiated on the electronic cassette 10.

Figure 1B:
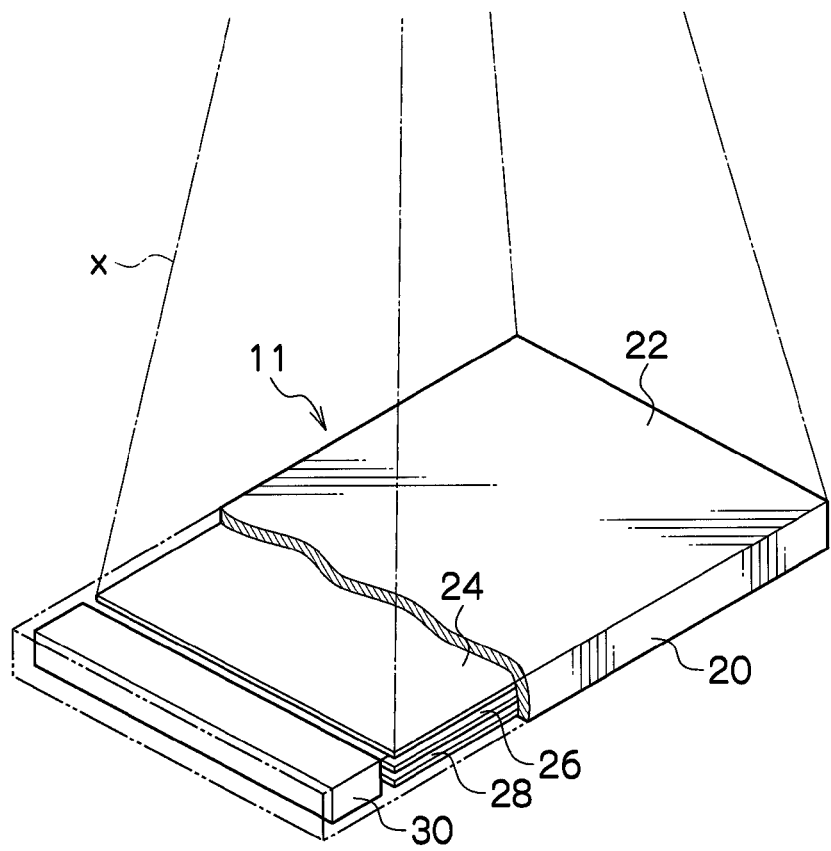
FIG. 1B is a schematic perspective view showing the internal structure of the electronic cassette.

The electronic cassette 10 includes a radiation detector 11 and a handle 16. As shown in FIG. 1B, the radiation detector 11 is covered by a tabular casing 20 having a certain thickness that contains a material that allows radiation X to be transmitted therethrough. Inside the casing 20, there are disposed, in order from an irradiated surface 22 side of the casing 20 that is irradiated with the radiation X, a grid 24 that removes scattered radiation of the radiation X that arises in accompaniment with the radiation X transmitting through the subject 19, a radiation detection panel 26 that detects the radiation X, and a lead plate 28 that absorbs back scattered radiation of the radiation X. Alternately, the irradiated surface 22 of the casing 20 may be configured by the grid 24. Further, a case 30 that houses various circuits including a microcomputer is disposed on one side of the interior of the casing 20. It is desirable to dispose a lead plate or the like on the side of the case 30 that is adjacent to the irradiated surface 22 in order to avoid the various circuits housed inside the case 30 to be damaged by being irradiated with the radiation X.

Figure 2:
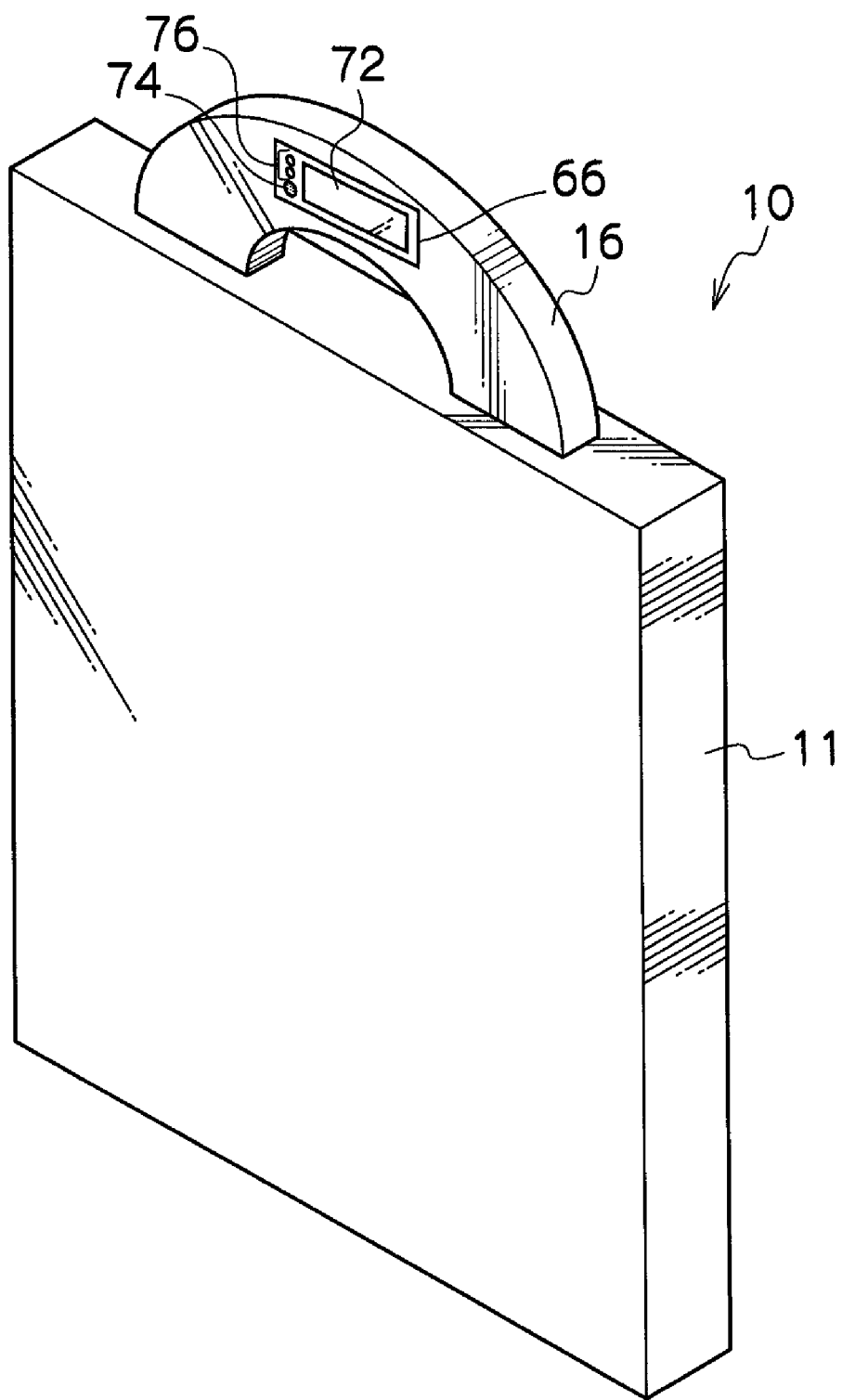
FIG. 2 is a perspective view showing the exterior of an electronic cassette of a first exemplary embodiment.

As shown in FIG. 2, the handle 16 functions as a grip for carrying the electronic cassette 10. A notification section 66 for giving notice of the operating state of the radiation detector 11 is provided at the handle 16. The notification section 66 has a touch panel display 72 for input of image capture conditions and the like and for display of the operating state of the radiation detector 11, a speaker 74 that outputs a buzzer sound or a message corresponding to the contents of notification, and plural LED lamps 76 that light-up in accordance with the contents of notification. LED lamps that have different light-emitting colors such as, for example, a red LED and a blue LED, or the like, can be used as the plural LED lamps 76.

The handle 16 is U-shaped in the exemplary embodiments. However, it suffices for the handle 16 to be a shape that functions as a grip, and the handle 16 may be T-shaped, substantially U-shaped, a shape with a hole that is circular or the like formed therein, or the like. Further, the handle 16 may be a structure that does not have pass-through hole, i.e., may be configured without a space in which a hand (a portion of a hand such as fingers or the like) can be inserted. For example, the handle 16 may be a handle at which is formed a concave portion that a hand (a portion of a hand such as fingers or the like) catches on, or a handle at which is formed a convex portion that can be grasped.

Figure 3:
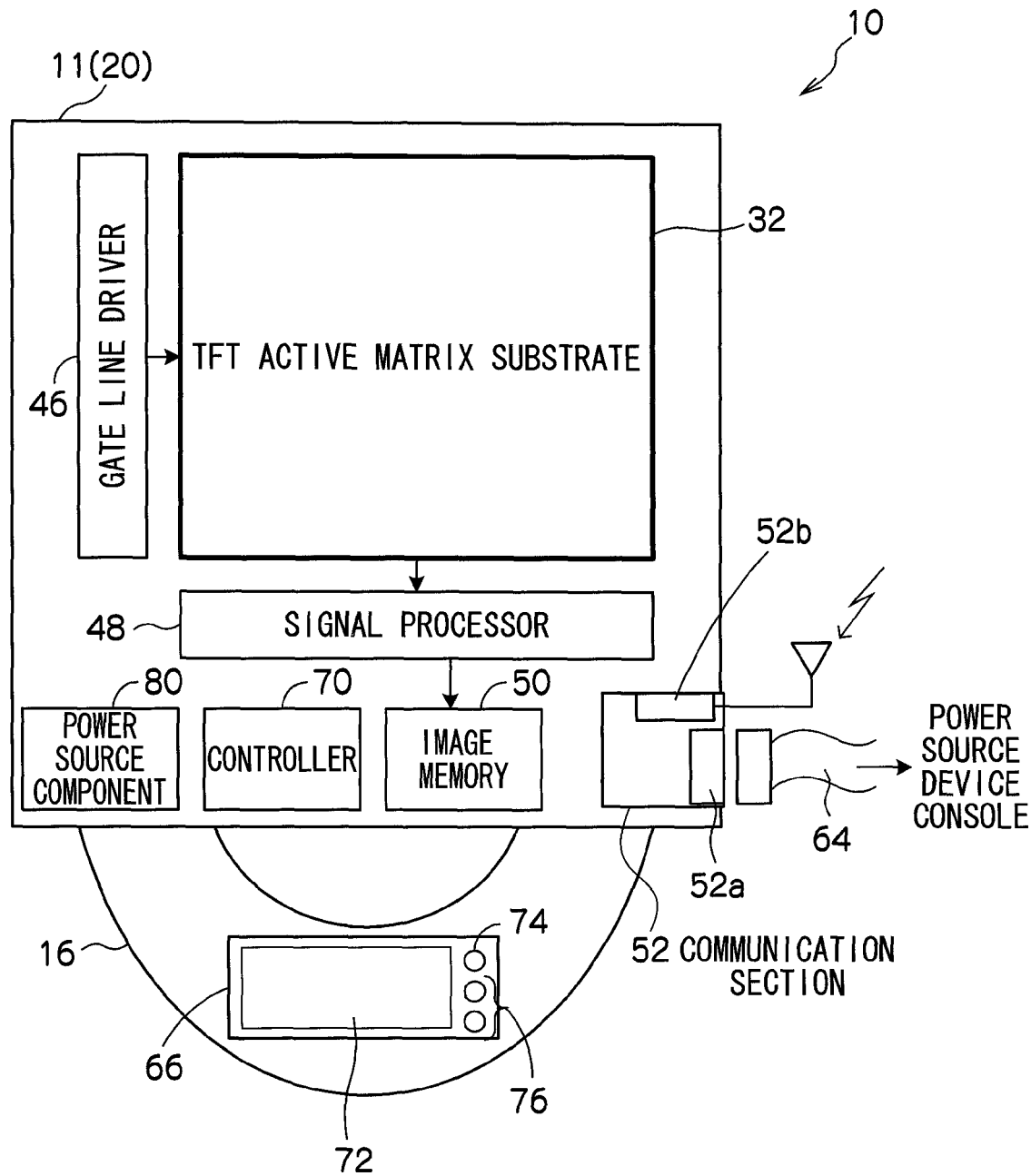
FIG. 3 is a block diagram showing the schematic structure of the electronic cassette of the first exemplary embodiment.

The radiation detector 11 is configured by a photoelectric conversion layer that absorbs and converts radiation into electric charges being applied on a TFT active matrix substrate 32 shown in FIG. 3. The photoelectric conversion layer is formed by, for example, non-crystalline a-Se (amorphous selenium) whose main component (e.g., having a content percentage equal to or greater than 50%) is selenium, and when the photoelectric conversion layer is irradiated with radiation, the photoelectric conversion layer converts the irradiated radiation into electric charges by generating, inside of itself, electric charges (electron-hole pairs) of charge amount corresponding to the radiation amount that is irradiated. Note that the radiation detector 11 is not limited to a structure that converts radiation directly into charges by using a radiation-charge converting material such as amorphous selenium or the like as described above. A structure may be employed that converts radiation into charges indirectly by carrying out conversion from radiation to light by a fluorescent material such as gadolinium oxysulfide (GOS) or cesium iodide (CsI) and carrying out conversion from light to charges using photoelectric conversion elements such as photodiodes.

On the TFT active matrix substrate 32, numerous pixels equipped with storage capacitors that store the electric charges generated by the photoelectric conversion layer and TFTs for reading the electric charges stored in the storage capacitors, are disposed in a matrix. The electric charges generated in the photoelectric conversion layer due to an irradiation of radiation onto the radiation detector 11 are stored in the storage capacitors of the individual pixels. Thus, the image information (data) that is carried in the radiation irradiated on the radiation detector 11 is converted into electric charge information and is held in the radiation detector 11.

Further, on the TFT active matrix substrate 32, there are disposed plural gate lines, which extend in a constant direction (row direction) and are for switching ON and OFF the TFTs of the individual pixels, and plural data lines, which extend in a direction (column direction) orthogonal to the gate lines and are for reading the stored electric charges from the storage capacitors via the TFTs that are switched ON. The individual gate lines are connected to a gate line driver 46, and the individual data lines are connected to a signal processor 48. When the electric charges are stored in the storage capacitors of the individual pixels, the TFTs of the individual pixels are switched ON in order in row units by signals supplied via the gate lines from the gate line driver 46, and the electric charges stored in the storage capacitors of the pixels whose TFTs are switched ON are transmitted through the data lines as electric charge signals and are inputted to the signal processor 48.

The signal processor 48 is equipped with amplifiers and sample/hold circuits that are disposed for each of the individual data lines. The electric charge signals transmitted through the individual data lines are amplified by the amplifiers and thereafter held in the sample/hold circuits. Multiplexers and A/D converters are connected to output ends of the sample/hold circuits in this order. The electric charge signals held in the individual sample/hold circuits are inputted in order (serially) to the multiplexers and are converted into digital image data by the A/D converters. An image memory 50 is connected to the signal processor 48, and the image data outputted from the A/D converters of the signal processor 48 are stored sequentially in the image memory 50.

Further, the radiation detector 11 has a controller 70 carrying out control of the radiation detector 11, a communication section 52 for carrying out communication with external devices such as a power source device, and/or a console, and a power source component 80 that supplies electric power to various circuits and elements in order to operate the electronic cassette 10.

The controller 70 is structured by a microcomputer that includes a CPU that governs control of the entire electronic cassette 10, a ROM serving as a storage medium in which are stored programs for radiographic image detection processing, image capture preparation processing, image capture processing, image data transmission processing and the like that will be described later, a RAM serving as a work area and temporarily storing data, and a memory serving as a storing section in which various types of information are stored. Note that the controller is not limited to controlling all of the operations of the device as in the exemplary embodiments, and may control some of the operations of the device.

The communication section 52 has a connector 52a for the connection of a coaxial cable 64 for carrying out power supply and data transfer, and a wireless communication section 52*b*. Wired communication is carried out when a cable is connected to the connector 52*a*, and wireless communication is carried out when a cable is not connected.

The power source component 80 can employ a structure that incorporates therein a battery (a chargeable secondary battery) and supplies electric power from the charged battery to the various circuits and element, so that the portability of the electronic cassette 10 is not adversely affected. A primary battery may be used as the battery, or the battery may be a structure that is usually connected to a commercial power source by a power cable connected to the connector 52*a* of the communication section 52, and rectifies and transforms the electric power supplied from the commercial power source, and supplies the electric power to the various circuits and elements. Note that the power source component is not limited to a structure that supplies electric power to all of the structural parts of the device as in the exemplary embodiments, and may supply electric power to some of the structural parts of the device. Further, the radiation detector 11 may be structured so as to have plural power source components.

Handling of the electronic cassette 10 will be described next.

Figure 4:
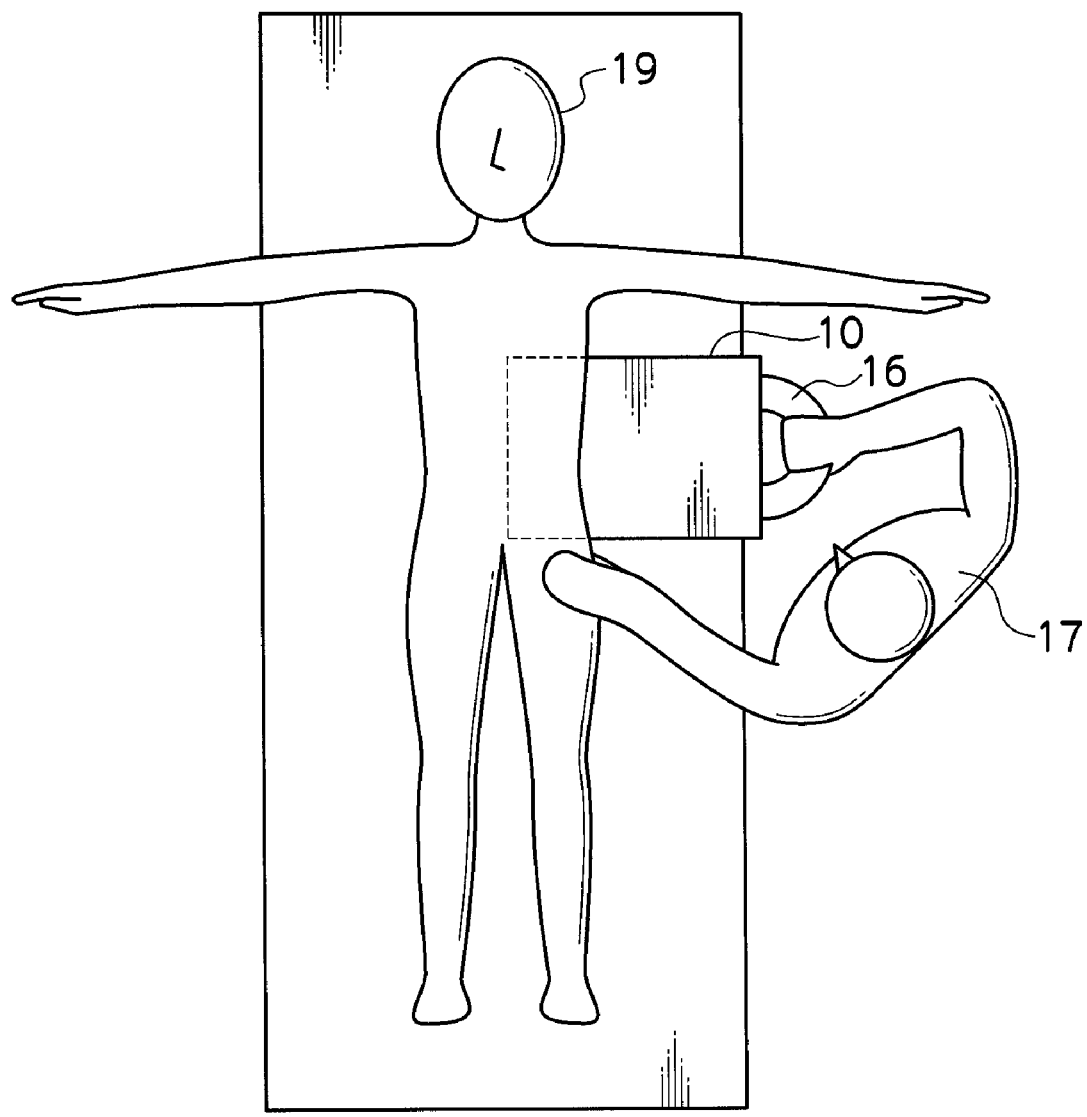
FIG. 4 is a drawing explaining handling of the electronic cassette.

For example, in a case in which the electronic cassette 10 is to be inserted between a bed and the subject 19, as shown in FIG. 4, an operator 17 of the electronic cassette 10 usually grasps the handle 16 and inserts the electronic cassette 10 between the bed and the subject 19 from the side opposite the side at which the handle 16 is provided.

Accordingly, because the handle 16 is being grasped by the operator 17, even during the time that the electronic cassette 10 is being inserted between the bed and the subject 19, the handle 16 is at a position that can be confirmed by the operator. After insertion as well, the handle 16 is not covered by the subject 19. Therefore, the operator 17 can easily confirm the notification section 66 that is provided at the handle 16.

Figure 5:
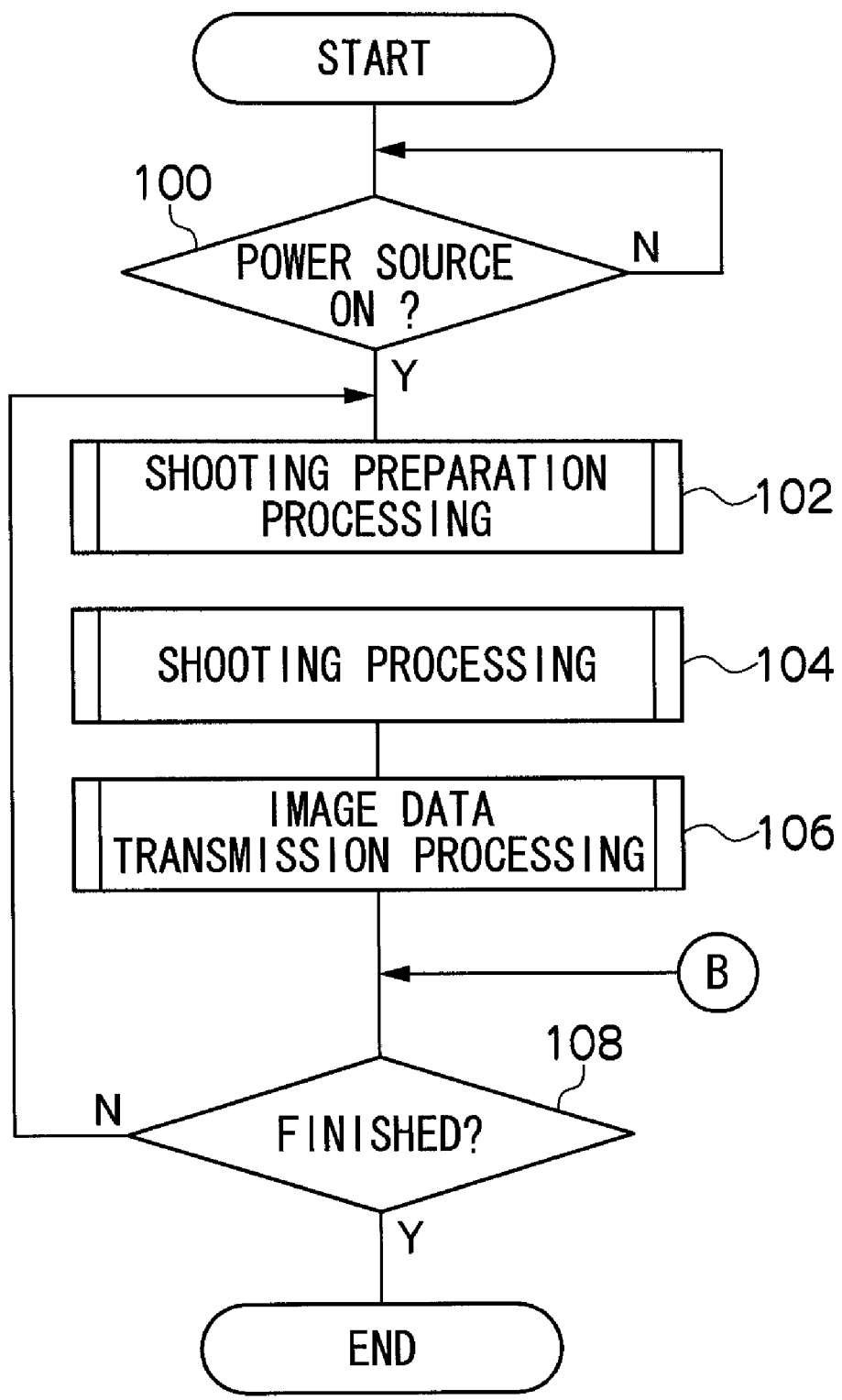
FIG. 5 is a flowchart showing a radiographic image detection processing routine in the first exemplary embodiment.

A radiographic image detection processing routine of the first exemplary embodiment will be described with reference to FIG. 5. This routine is executed by the CPU of the controller 70.

In step 100, it is determined whether or not the power source of the electronic cassette 10 has been turned on. This determination is carried out in accordance with whether or not a power source on signal, that is generated by an unillustrated power source switch provided at the electronic cassette 10 being turned on, is received. If the power source has been turned on, the routine proceeds to step 102, whereas if the power source has not been turned on, the routine stands-by until the power source is turned on.

In step 102, image capture preparation processing that will be described later is executed. In step 104, image capture processing that will be described later is executed. In step 106, image data transmission processing that will be described later is executed.

In step 108, it is determined whether or not processing has ended. This determination determines that processing has ended when a power off signal, that is generated by the power source switch being turned off, is received, or if a predetermined time period elapses in a state in which no operation is carried out with respect to the electronic cassette 10, or the like. If the processing has not ended, the routine returns to step 102. If processing has ended, the power source of the electronic cassette 10 is turned off and processing ends.

Figure 6:
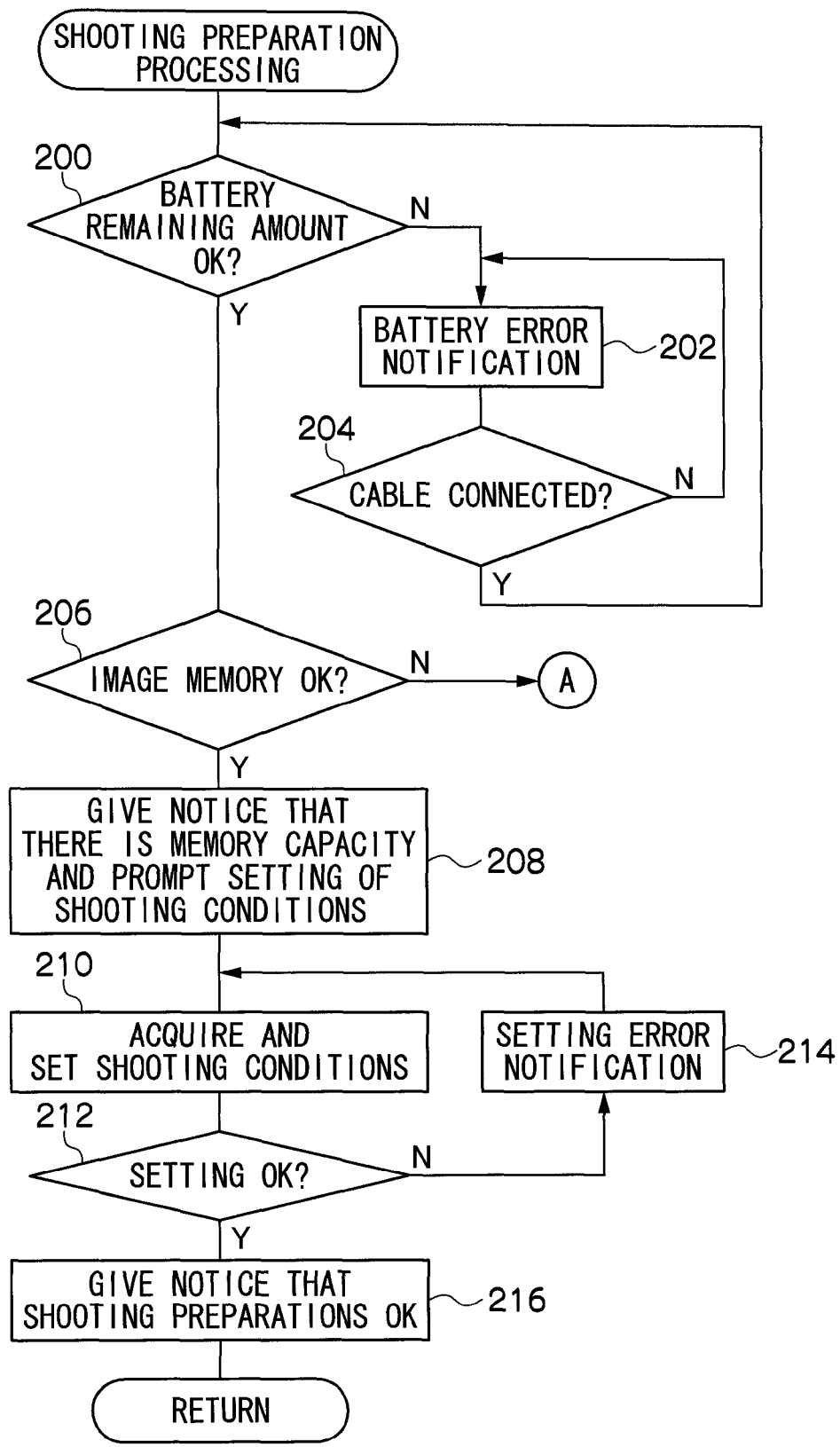
FIG. 6 is a flowchart showing an image capture preparation processing routine in the first exemplary embodiment.

The image capture preparation processing routine, that is executed in step 102 of the radiographic image detection processing routine in the first exemplary embodiment, will be described next with reference to FIG. 6.

In step 200, it is determined whether or not, for the battery remaining amount that is the amount of electric power stored in the power source component 80, an amount of electric power that is needed in order to carry out radiographic image capture is stored. If the needed amount of electric power is stored, the routine advances to step 206. If the needed amount of electric power is not stored, the routine moves on to step 202, and the user is notified that the battery remaining amount is insufficient. This notification may be carried out by displaying a message on the touch panel display 72, lighting the LED lamps 76, outputting a buzzer sound from a speaker 74, or the like.

In step 204, it is determined whether or not the coaxial cable 64 is connected to the connector 52*a* of the communication section 52. This determination is carried out by detecting the output of the signal line from the coaxial cable 64. If connection is detected, the routine returns to step 200, and the absence/presence of the battery remaining amount is determined again. If connection is not detected, the routine returns to step 202, and notification of a battery error is continued.

In step 206, it is determined whether or not the image memory 50 has the free space that is needed in order to carry out the next radiation shooting. The free space of the image memory 50 that is needed for image capture differs in accordance with the image capture conditions, such as the size of the image data. Thus, for example, image capture conditions requiring the maximum free space may be assumed, and the free space that is needed in this case may be set as a threshold value, and determination may be carried out by comparing this threshold value and the current free space of the image memory 50. If there is the needed free space, the routine proceeds to step 208 where the user is notified that the image memory 50 has the needed free space and is prompted to set the image capture conditions. If the image memory 50 does not have free space, the routine moves on to step 400 of the image data transmission processing that will be described later.

In step 210, the information, such as the image capture conditions that may be inputted by the touch panel display 72 being operated, are acquired. Alternatively, the information, such as the image capture conditions, may be acquired from a console that is connected via the communication section 52. Note that the electronic cassette 10 is connected with the console by wired communication if a cable is connected to the connector 52*a* of the communication section 52, and by wireless communication if a cable is not connected. The acquired information, such as the image capture conditions, are stored in a predetermined region, and setting of various parameters, and the like, are carried out. The image capture information may include information such as the radiation irradiating time period, the size of the image data.

In step 212, it is determined whether or not the image capture conditions are set normally. In cases such as contents that are outside of the set ranges are inputted, or the information such as the image capture conditions cannot be acquired due to a poor communication state or other reasons, it is determined that the image capture conditions are not set normally, and the routine moves on to step 214. In step 214, the user is notified that the image capture conditions were not set normally and is prompted to set the image capture conditions again, and the routine returns to step 210.

If the image capture conditions are set normally, the routine advances to step 216 where the user is notified that the image capture conditions have been set normally and the electronic cassette 10 is in a standby state in which the preparations for capturing (shooting) have been completed, and the routine returns to the radiographic image detection processing routine.

Figure 7:
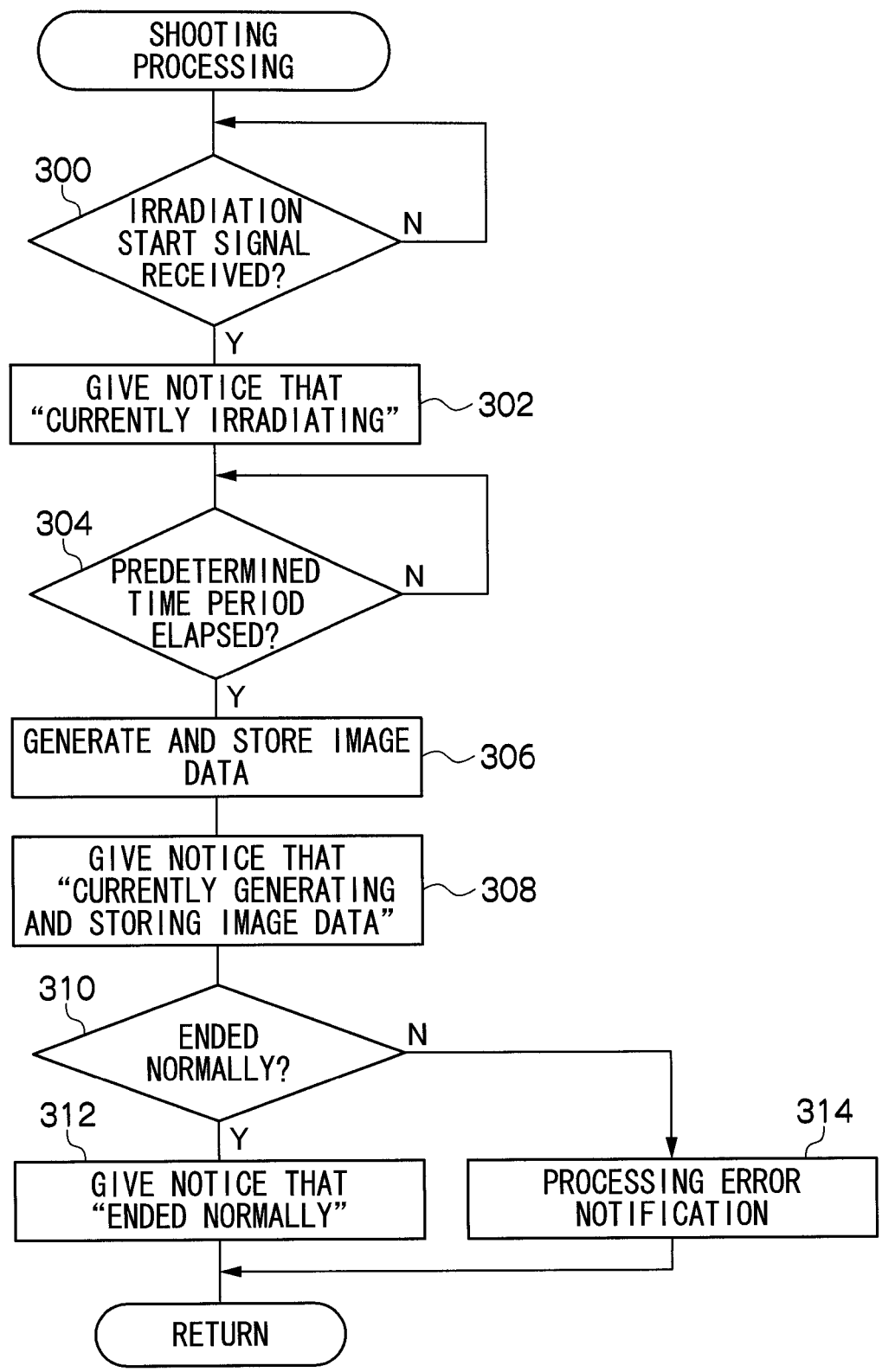
FIG. 7 is a flowchart showing an image capture processing routine in the first exemplary embodiment.

The image capture processing routine, that is executed in step 104 of the radiographic image detection processing routine in the first exemplary embodiment, will be described next with reference to FIG. 7.

In step 300, it is determined whether or not irradiation of radiation has started. This determination determines whether or not the electronic cassette 10 has received a radiation irradiation start signal, that is transmitted to the electronic cassette 10 as well, at the time that the radiation irradiation start signal is transmitted from an external device to the radiation generator 18 by a radiation irradiation start switch being turned on. If the start signal is received, the routine moves on to step 302 and the user is notified that radiation of irradiation is currently being carried out. If the irradiation start signal is not received, the routine stands-by until the signal is received.

In step 304, by referring to the image capture conditions that were stored in step 210 of the above-described image capture preparation processing, it is determined whether or not the predetermined radiation irradiation time period has elapsed. If the time period has not elapsed, the routine stands-by until it does elapse. When the time period has elapsed, the routine moves on to step 306, the charges accumulated by the irradiation of the radiation are read-out, image data is generated, and the generated image data is stored in the image memory 50. When the processing of step 306 starts, immediately in next step 308, the user is notified that image data is currently being generated and stored.

In step 310, it is determined whether or not the processing of generating and storing image data has finished normally. If the processing has finished normally, the routine moves on to step 312, and the user is notified that the processing has finished normally. If the processing has not finished normally, the routine moves on to step 314 where the user is notified that the processing did not finish normally, and the routine returns to the radiographic image detection processing routine. Note that, in step 314, the user can be notified also of the cause of the processing not finishing normally (the contents of the error).

Figure 8:
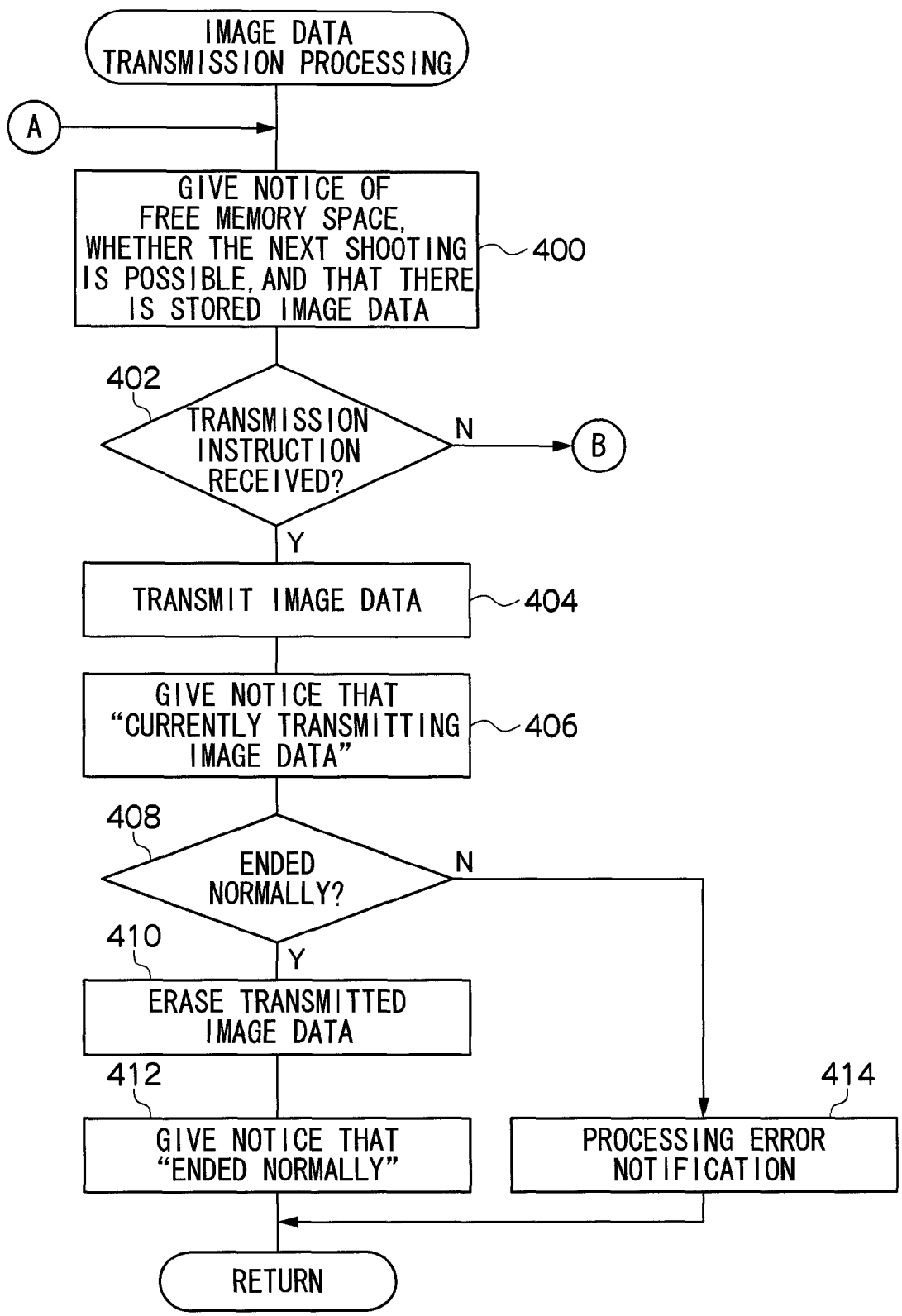
FIG. 8 is a flowchart showing an image data transmission processing routine in the first exemplary embodiment.

The image data transmission processing, that is executed in step 106 of the radiographic image detection processing routine in the first exemplary embodiment, will be described with reference to FIG. 8.

In step 400, the user is notified of the free memory space of the image memory 50, and whether or not that free space is an amount needed for the next shooting, and of the absence/presence of image data stored in the image memory 50.

In step 402, it is determined whether or not an instruction to transmit image data from the electronic cassette 10 to the console has been received, from a signal that is inputted by operation of the touch panel display 72 or by a signal that is transmitted from the console connected via the communication section 52. If an instruction is received, the routine move on to step 404. If an instruction is not received, the routine moves on to step 108 of the radiographic image detection processing routine.

In step 404, the image data is read-out from the image memory 50, and is transmitted to the connected console. When the processing of step 404 starts, immediately in step 406, the user is notified that image data is currently being transmitted.

In step 408, it is determined whether or not transmission of the image data has finished normally. If transmission has finished normally, the routine proceeds to step 410, and the transmitted image data is erased from the image memory 50.

In step 412, the user is notified that transmission of the image data has finished normally. If transmission of the image data did not finish normally, the routine moves on to step 414 where the user is notified that transmission did not finish normally, and the routine returns to the radiographic image detection processing routine. Note that, in step 414, the user can also be notified of the cause of the transmission not finishing normally (the contents of the error).

As described above, in accordance with the electronic cassette of the first exemplary embodiment, by providing the notification section, that is for giving notice of the operating state of the electronic cassette, at the handle that is not covered by the subject, the operating state of the electronic cassette can be easily confirmed. Further, at the electronic cassette of the first exemplary embodiment, the touch panel display that functions as the notification section and an input section is provided at the handle. Namely, by providing the input section as well at the handle that is not covered by the subject, inputting of the image capture conditions and the like also can be carried out easily. In particular, at times of carrying out re-capturing, setting of the image capture conditions can be carried out without imposing on the subject.

Note that the order of the processings of the respective steps of the radiographic image detection processing, the image capture preparation processing, the image capture processing and the image data transmission processing in the first exemplary embodiment are not limited to the above-described order. It suffices to be able to give notice of the current state of the electronic cassette, information regarding errors, and other information, in accordance with the operating state of the electronic cassette.

An electronic cassette relating to a second exemplary embodiment will be described next. The first exemplary embodiment describes a case in which, at the electronic cassette 10, the handle 16 is provided at the radiation detector 11, i.e., a case in which the radiation detector 11 and the handle 16 are integral. The second exemplary embodiment differs with regard to the point that the handle can be attached to and detached from the radiation detector. Note that structures that are the same as those of the electronic cassette of the first exemplary embodiment are denoted by the same reference numerals, and description thereof is omitted.

Figure 9:
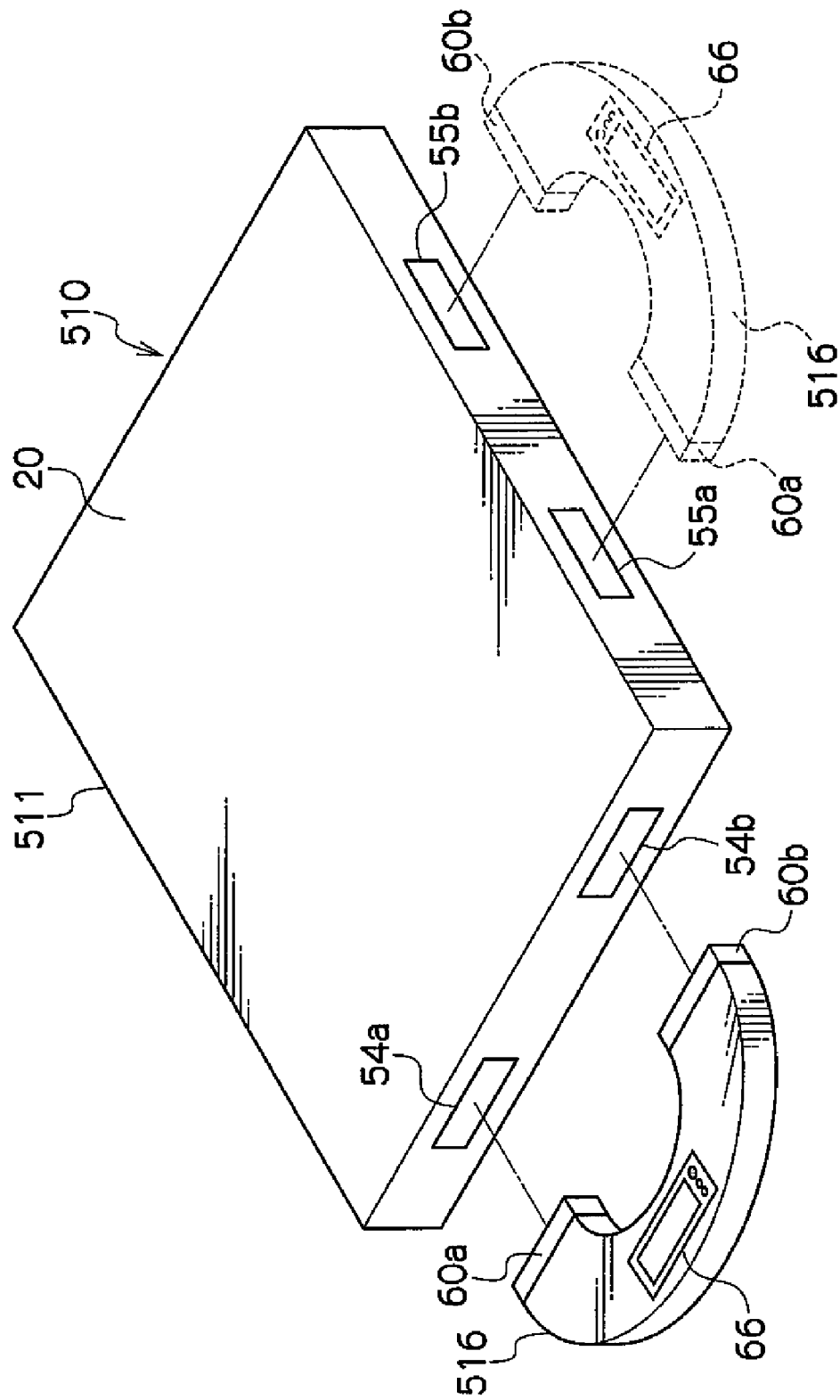
FIG. 9 is a perspective view showing the exterior of an electronic cassette of a second exemplary embodiment.

As shown in FIG. 9, an electronic cassette 510 relating to the second exemplary embodiment is structured by a radiation detector 511 and a handle 516 that can be attached to and detached from the radiation detector 511.

The handle 516 has mounting portions 60a, 60b for mounting to the radiation detector 511. On the other hand, mounting portions 54a, 54b, to which the mounting portions 60a, 60b of the handle 516 can be detachably connected, are provided at a short-side side surface of the radiation detector 511 that is rectangular as seen in plan view. Mounting portions 55a, 55b, to which the mounting portions 60a, 60b of the handle 516 can be detachably connected, are provided at a long-side side surface of the radiation detector 511. Due thereto, the handle 516 can be detachably attached to the radiation detector 511, and, in a state of being mounted to the radiation detector 511, functions as a grip of the electronic cassette 510. Note that the mounting portions for mounting the handle 516 are not limited to being provided at two of the side surfaces of the casing 20 of the radiation detector 511, and may be provided at any one side, or at three or four sides.

Figure 10:
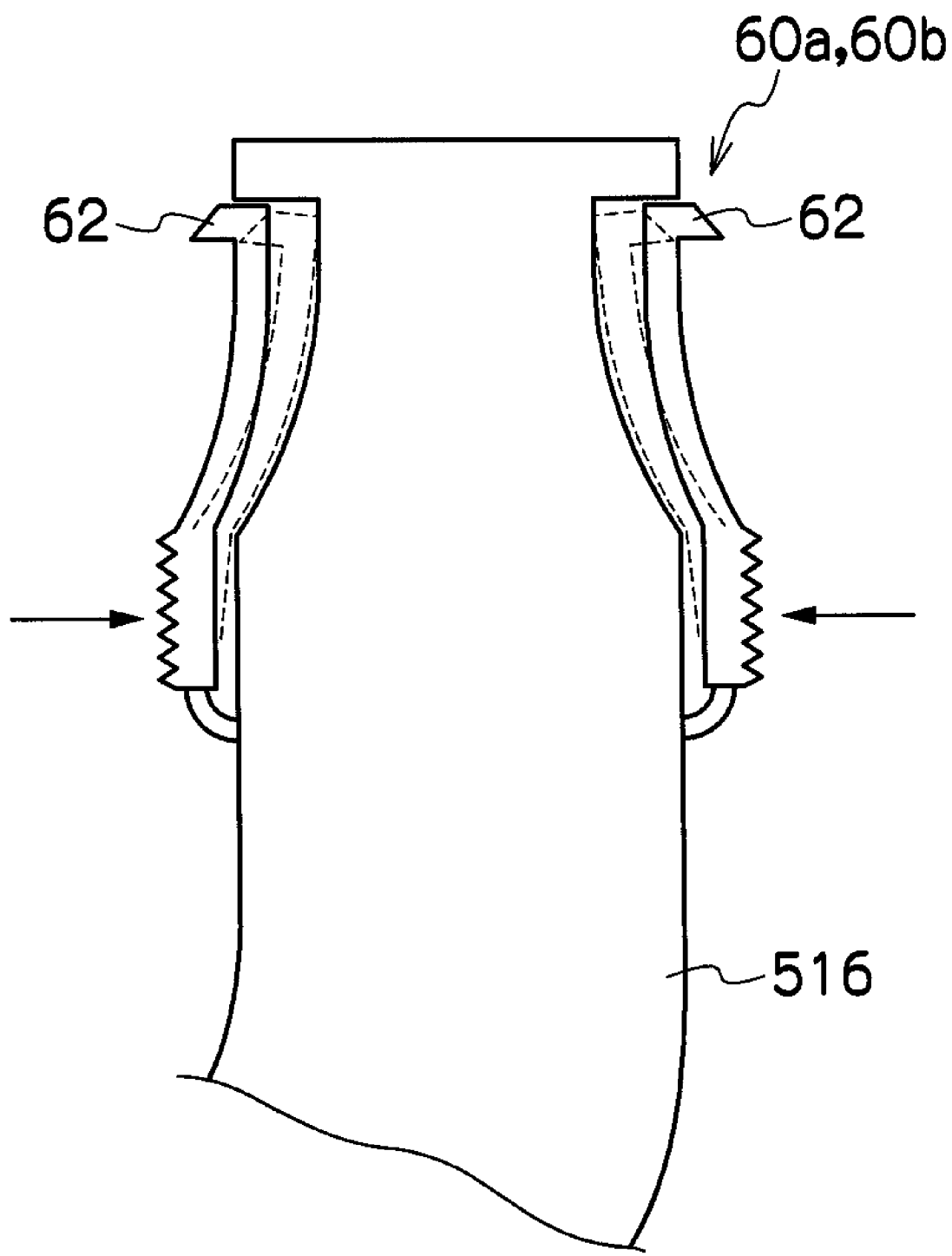
FIG. 10 is a schematic drawing showing a handle mounting portion of the electronic cassette of the second exemplary embodiment.

The mounting portions 54a, 54b, 55a, 55b of the radiation detector 511 are formed in the casing 20 as holes for the insertion of the mounting portions 60a, 60b of the handle 516. As shown in FIG. 10, at the side surfaces of the handle 516, the mounting portions 60a, 60b of the handle 516 have stoppers 62 whose distal ends are shaped like hooks and that are mounted to the handle 516 main body by elastic members. In the usual state, the hook-shaped distal ends of the stoppers 62 are positioned so as to project-out from the width of the handle 516. Due to the portions pointed by arrows shown in FIG. 10 being pushed, the stoppers 62 are accommodated within the range of the width of the handle 516. In the state in which the mounting portions 60a, 60b of the handle 516 are inserted in the mounting portions 54a, 54b, 55a, 55b of the radiation detector 511, the hook-shaped distal ends of the stoppers 62 engage with the holes of the casing 20 that are formed as the mounting portions 54a, 54b, 55a, 55b of the radiation detector 511, and the handle 516 is thereby mounted to the radiation detector 511.

Note that the holes of the casing 20 that are formed as the mounting portions 54a, 54b, 55a, 55b of the radiation detector 511 function also as ventilation holes for ventilating the air within the radiation detector 511. Because the mounting portions are provided at the long-side side surface and the short-side side surface of the electronic cassette 510, when the handle 516 is mounted to the mounting portions 55a, 55b at the long-side side surface, the mounting portions 54a, 54b of the short-side side surface become the ventilation holes, and when the handle 516 is mounted to the mounting portions 54a, 54b of the short-side side surface, the mounting portions 55a, 55b of the long-side side surface become the ventilation holes.

Figure 11:
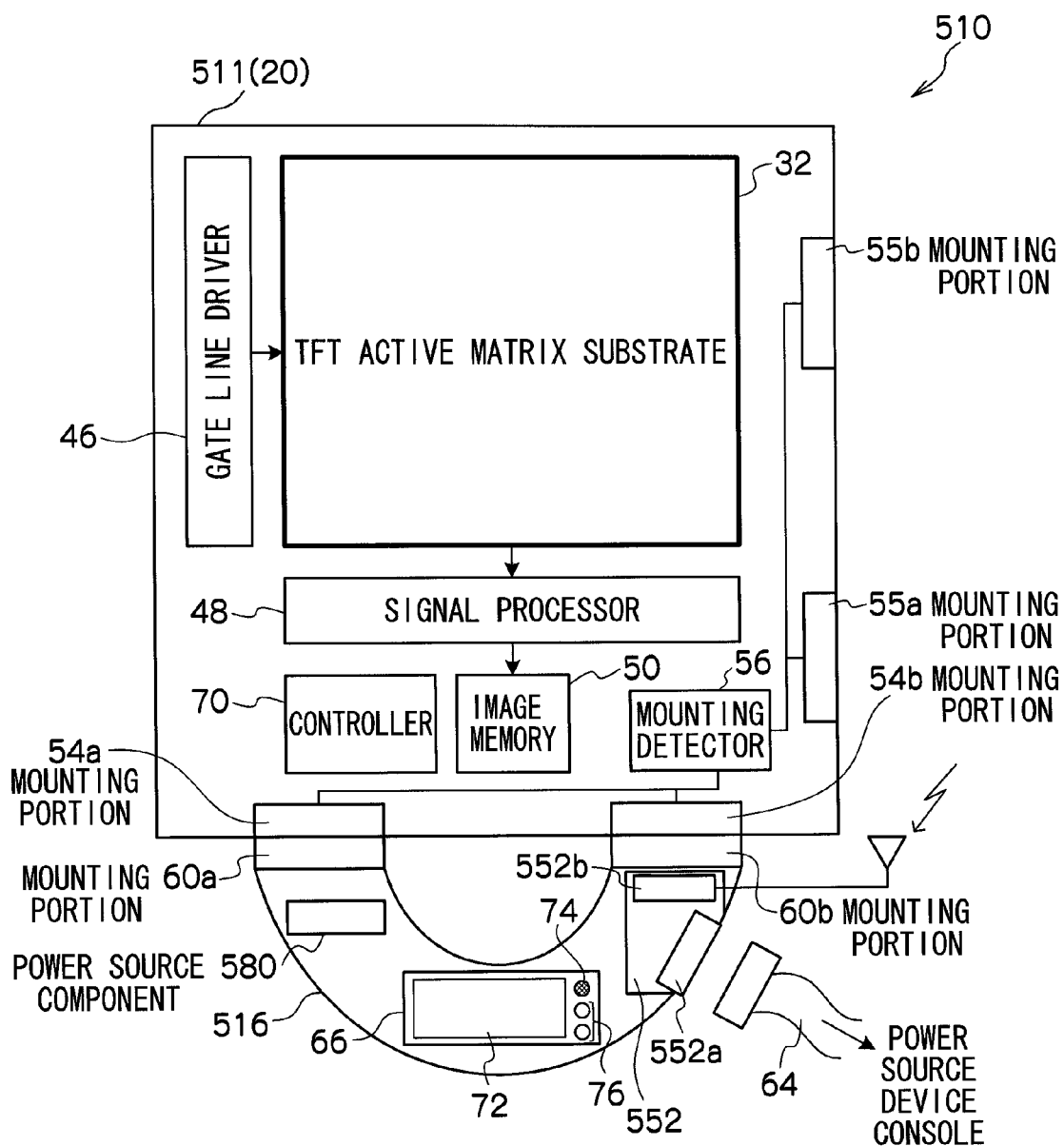
FIG. 11 is a block diagram showing the schematic structure of the electronic cassette of the second exemplary embodiment.

As shown in FIG. 11, the electronic cassette 510 has, in the radiation detector 511, a mounting detector 56 that detects whether or not the handle 516 is mounted to the radiation detector 511. The electronic cassette 510 has, in the handle 516, a communication section 552 and a power source component 580.

The mounting detector 56 is connected to the mounting portions 54a, 54b, 55a, 55b, and a signal line from the handle 516 with respect to the radiation detector 511 is provided for each of the mounting portions 54a, 54b of the short-side side surface and the mounting portions 55a, 55b of the long-side side surface. By detecting the outputs of the signal lines, the mounting detector 56 detects whether or not the handle 516 is mounted to the radiation detector 511, and further, which of the mounting portions of the short-side side surface or of the long-side side surface the handle 516 is mounted to. Note that the mounting detection section may be structured so as to detect whether or not the handle 516 is mounted to the radiation detector 511 by utilizing light such as infrared rays, or the electrostatic effect (e.g., a method of detecting, by the electrostatic capacity, whether or not an inductor is near). Or, the mounting detection section may be structured so as to detect, by sensors, that the mounting portions of both have reached predetermined positions.

Here, the relationship between the orientation of the electronic cassette 510 at the time of capturing (shooting), and the mounted position of the handle 516 to the radiation detector 511, will be described.

Figure 12A:
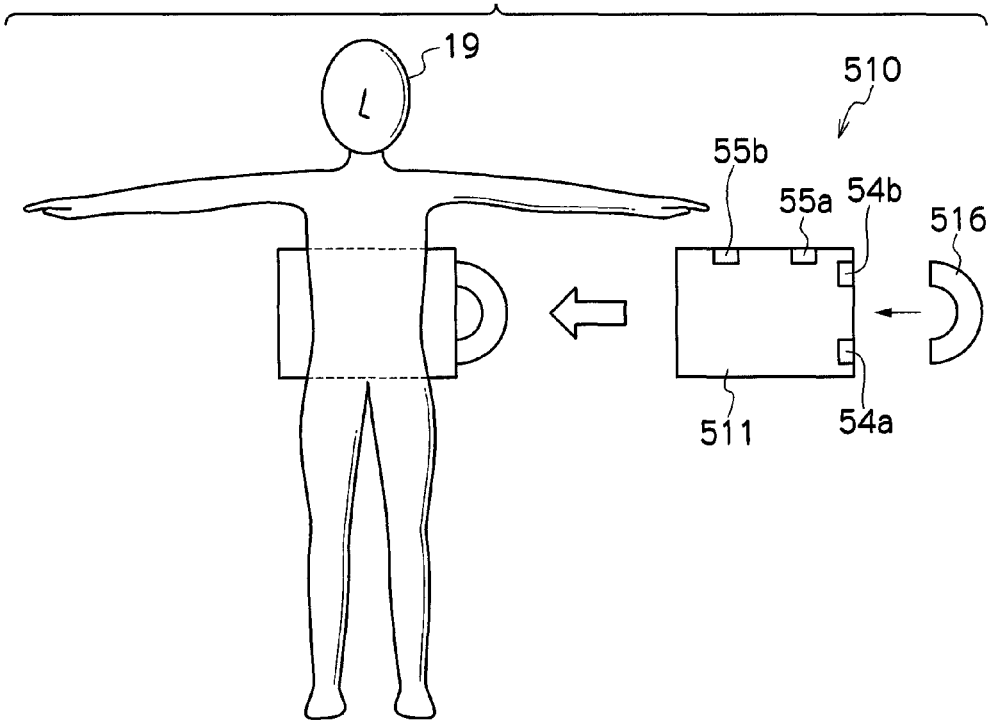
FIG. 12A is a drawing showing lateral placement of the electronic cassette.
Figure 12B:
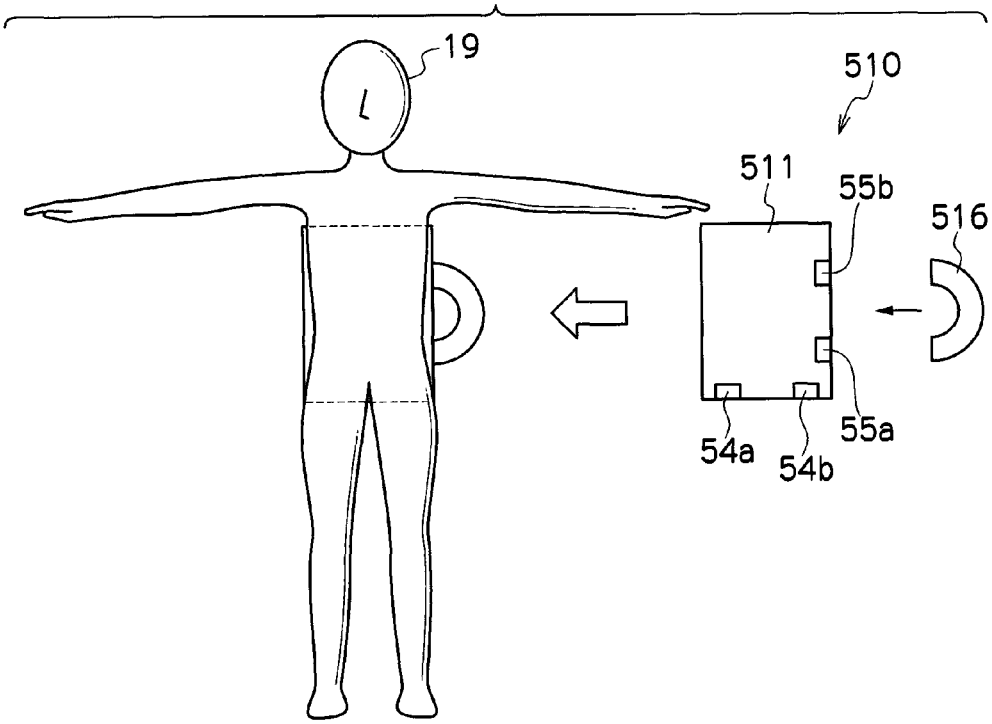
FIG. 12B is a drawing showing vertical placement of the electronic cassette.

As shown in FIG. 12A, the arrangement in which the direction orthogonal to the head-to-toe direction (the direction from the head toward the feet) of the subject 19, and the long sides of the electronic cassette 510, are orthogonal is called "lateral placement". As shown in FIG. 12B, the arrangement in which the head-to-toe direction of the subject 19 and the long sides of the electronic cassette 510 are parallel is called "vertical placement".

As shown in FIG. 4, the electronic cassette 510 can be handled such that the operator 17 grasps the handle 516 and inserts the electronic cassette 510 between the bed and the subject 19 from the side opposite the side at which the handle 516 is provided. Accordingly, in the case of lateral placement, the handle 516 is mounted to a short-side side surface of the radiation detector 511, and, in the case of vertical placement, the handle 516 is mounted to a long-side side surface of the radiation detector 511.

The mounted position of the handle 516 that is detected at the mounting detector 56 can be stored in association with the generated image data, and for example, the notification section 66 can notify the user of the mounted position of the handle at the time of previous shooting, or, notify the user, if the mounted position of the handle is different at the time of the current shooting and the time of the previous shooting, that the mounted position of the handle is different. Further, image processing, such as rotating the generated image data, may be performed on the basis of the mounted position of the handle. In this case, the notification section 66 may give notice that image processing has been performed.

As described above, in accordance with the electronic cassette of the second exemplary embodiment, both in cases in which the electronic cassette is placed vertically and laterally, the handle can be mounted to a position at which it is easy to use. Because the notification section for giving notice of the operating state of the electronic cassette is provided at the handle, the operating state of the electronic cassette can be confirmed easily regardless of the orientation of the electronic cassette at the time of shooting. Further, the handle is not covered by the subject both when the orientation of the electronic cassette is vertical placement and when the orientation is horizontal placement. Because the communication section is provided at the handle, in the case of wired communication, connection of a coaxial cable with the connector provided at the handle is easy, and, in the case of wireless communication, poor propagation due to effects of the body can be prevented.

Note that, in the electronic cassettes of the first and second exemplary embodiments, the notification section is structured by a touch panel display, a speaker and LED lamps. However, the structure of the notification section is not limited to this and the notification section may be structured by any single one of the touch panel display, the speaker and the LED lamps, or may be structured by the touch panel display and the speaker, or by the touch panel display and the LED lamps, or by the speaker and the LED lamps. Further, the input device may be structured by switches or cursor keys or the like.

The first exemplary embodiment describes a case in which the communication section and the power source component are provided at the radiation detector of the electronic cassette. The second exemplary embodiment describes a case in which the communication section and the power source component are provided at the handle of the electronic cassette. However, embodiments are not limited to these structures and the communication section and the power source component may be provided at either of the radiation detector and the handle. For example, the electronic cassette may be structured such that the communication section is provided at the radiation detector and the power source component is provided at the handle. Alternatively, the electronic cassette may be structured such that the power source component is provided at the radiation detector and the communication section is provided at the handle.

Further, in the first and second exemplary embodiments, examples are described in which the coaxial cable 64 is connected to the electronic cassette, and supply of electric power to the radiation detector and/or transmitting and receiving of data such as the image capture conditions and the image data between the radiation detector and a controller such as a console is performed via the coaxial cable 64. However, the embodiments are not limited to these.

For example, in a case in which the handle 516 is detachable with respect to the radiation detector 511 as in the second exemplary embodiment, data such as the image capture conditions and the image data can be exchanged between the radiation detector 511 and the console via the handle 516. In this case, a memory is provided in the handle 516.

Figure 13:
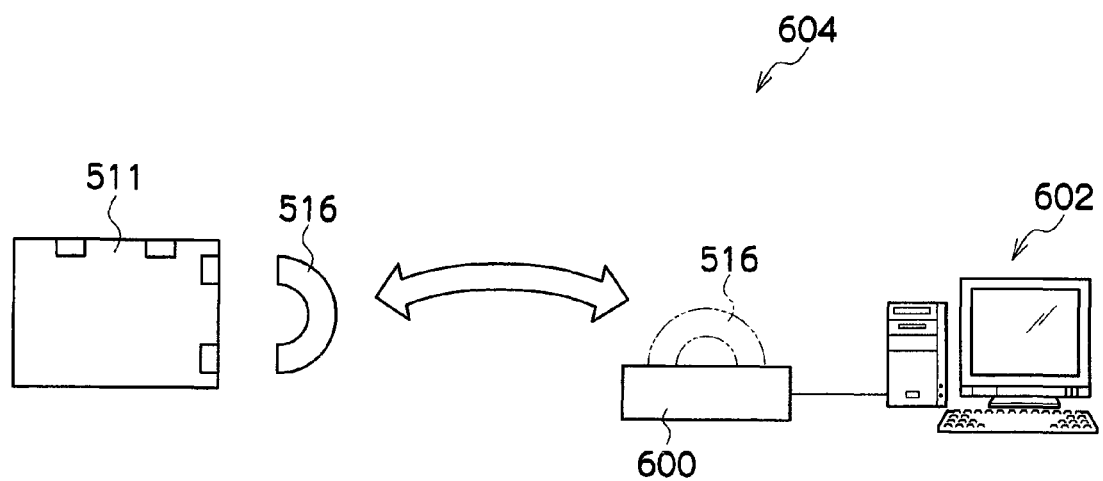
FIG. 13 is a block diagram showing the configuration of a radiographic image detection system including the electronic cassette, a cradle, and a console according to another exemplary embodiment.

Further, as shown in FIG. 13, a cradle 600 can be provided that can accommodate the handle 516 in a detachable manner and that enables access to the memory in the accommodated handle 516. The cradle 600 can be connected to the console 602, and the console 602 can be configured to access the memory in the handle 516 when the handle 516 is mounted on (accommodated in) the cradle 600.

When performing an image capture operation, the operator 17 detaches the handle 516 from the radiation detector 511 and attaches the handle 516 to the cradle 600. The console 602 stores the image capture conditions in the memory in the handle 516 via the cradle 600. The operator 17 then detaches the handle 516 in which the image capture conditions are stored from the cradle 600 and attaches the handle 516 to the radiation detector 511 which performs the image capture. The radiation detector 511 reads out the image capture conditions from the memory of the handle 516.

After the image capture operation, the radiation detector 511 stores the generated image data in the memory of the handle 516. The operator 17 detaches the handle 516 from the radiation detector 511 and attaches the handle 516 to the cradle 600. The console 602 reads out the image data from the memory of the handle 516 via the cradle 600. Thus, a radiographic image detection system 604 can be configured to include the electronic cassette as the radiographic image detection device, the cradle 600 as a handle accommodating device, and the console 602 as the controller, and image capture conditions and image data can be exchanged between the radiation detector 511 and the console 602 via the handle 516.

In the radiographic image detection system 604, the handle 516 may supply electric power to the radiation detector 511. In this case, a battery is provided in the handle 516 and the battery can be charged via the cradle 600. The radiation detector 511 may be directly driven by the battery in the handle 516. Alternatively, a power source component may be also provided in the radiation detector 511 (for example, the power source component 80 provided in the first exemplary embodiment) for driving the radiation detector 511, and the battery in the handle 516 may be provided for charging the power source component 80 of the radiation detector 511. The battery provided in the handle may be a capacitor with which rapid charging is possible.

Figure 14:
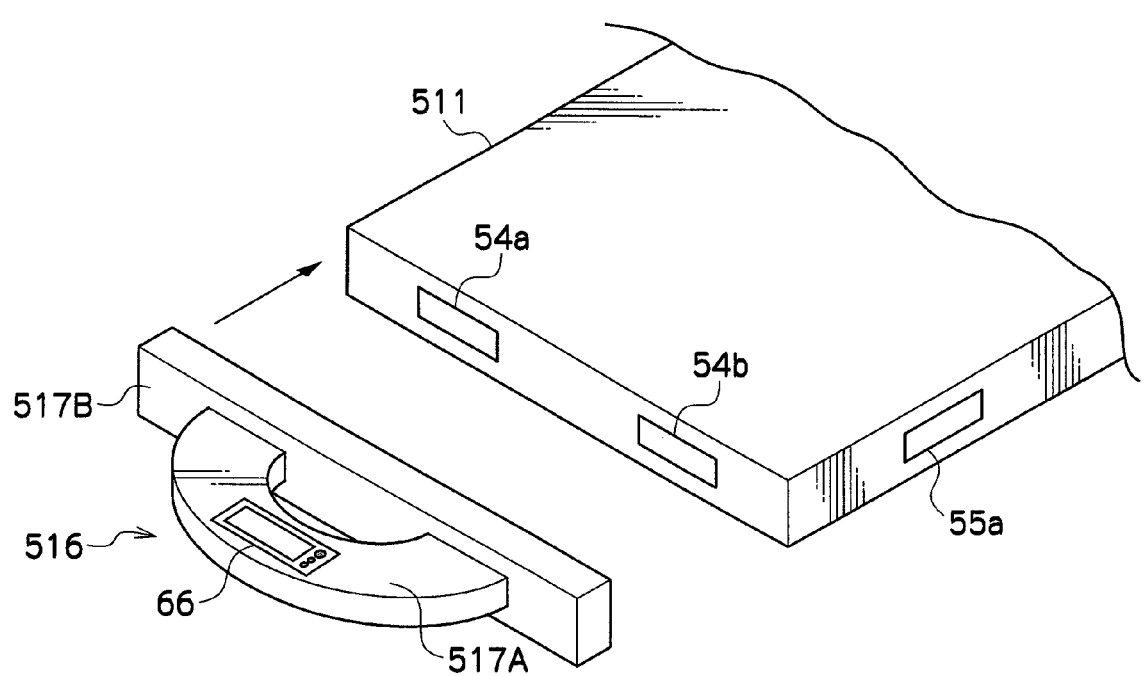
FIG. 14 is a perspective view showing an example of a shape of the handle in the another exemplary embodiment.
Figure 15:
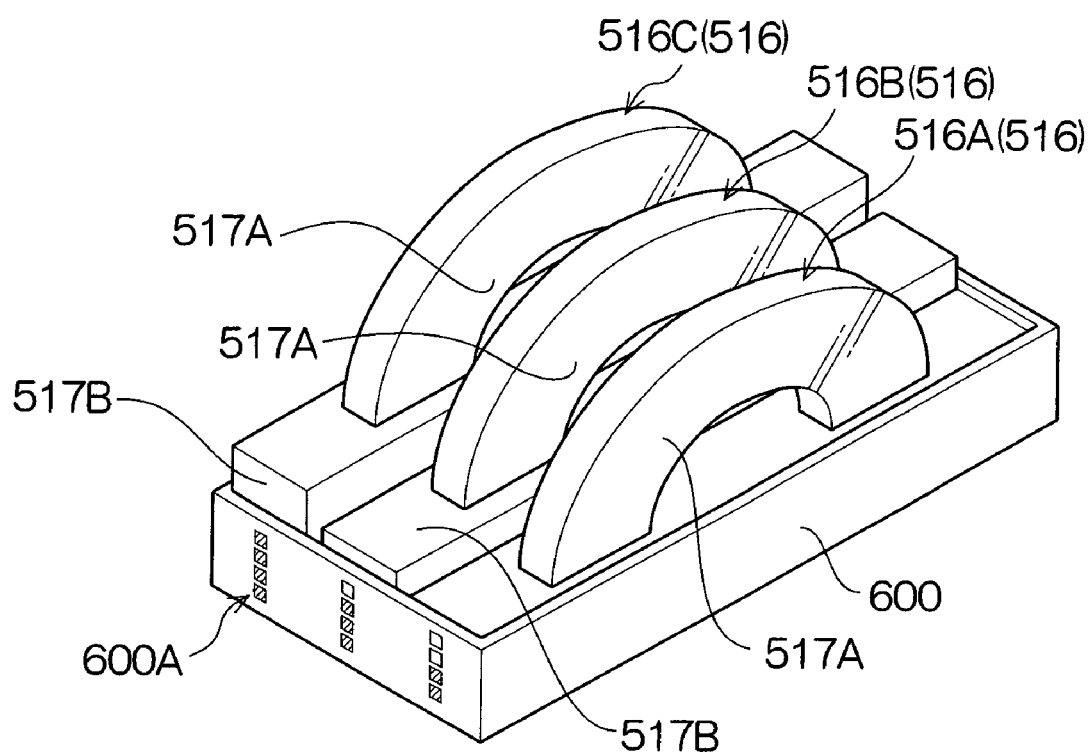
FIG. 15 is a perspective view showing an example of the cradle which can accommodate plural handles having different shapes.

Furthermore, in the first and second exemplary embodiments, examples are described in which, as shown in FIG. 9, the U-shaped portion where the user grasps is detached from the radiation detector 511 as the handle 516. However, the embodiments are not limited to these. For example, as shown in FIG. 14, the handle 516 may be formed in a substantial D-shape, which is formed by a U-shaped portion 517A grasped by a user, and a plate-shaped portion 517B connected with the both ends of the U-shaped portion 517A. As shown in FIG. 15, the handle 516 may be formed in various shapes such as a handle 516A formed only by the U-shaped portion 517A, a handle 516B formed by the U-shaped portion 517A and the plate-shaped portion 517B having relatively small thickness, and a handle 516C formed by the U-shaped portion 517A and the plate-shaped portion 517B having relatively large thickness. For example, the handle 516A may incorporate a battery having small capacity, is only possible to capture small number of radiographic images, but is made to be light weight. The handle 516B may incorporate a battery having medium capacity, and is possible to capture relatively larger number of radiographic images. The handle 516B may incorporate a battery having large capacity, and is possible to capture large number of radiographic images. The user may select a handle from these handles depending on the intended use.

The cradle 600 may accommodate plural handles 516 having different shapes. In the configuration in which the radiation detector 511 is driven with electronic power supplied from the power source component 80 provided therein, and the power source component 80 is charged by the battery incorporated in the handle 516, a hot-swap function may be realized by replacing, when the remaining battery level become low, the handle 516 with another handle 516 which has been charged, in order to extend the operation time period. Note that the cradle 600 shown in FIG. 600 is provided with a display section 600A which displays the charge level of the battery in the handle 516.

Figure 16:
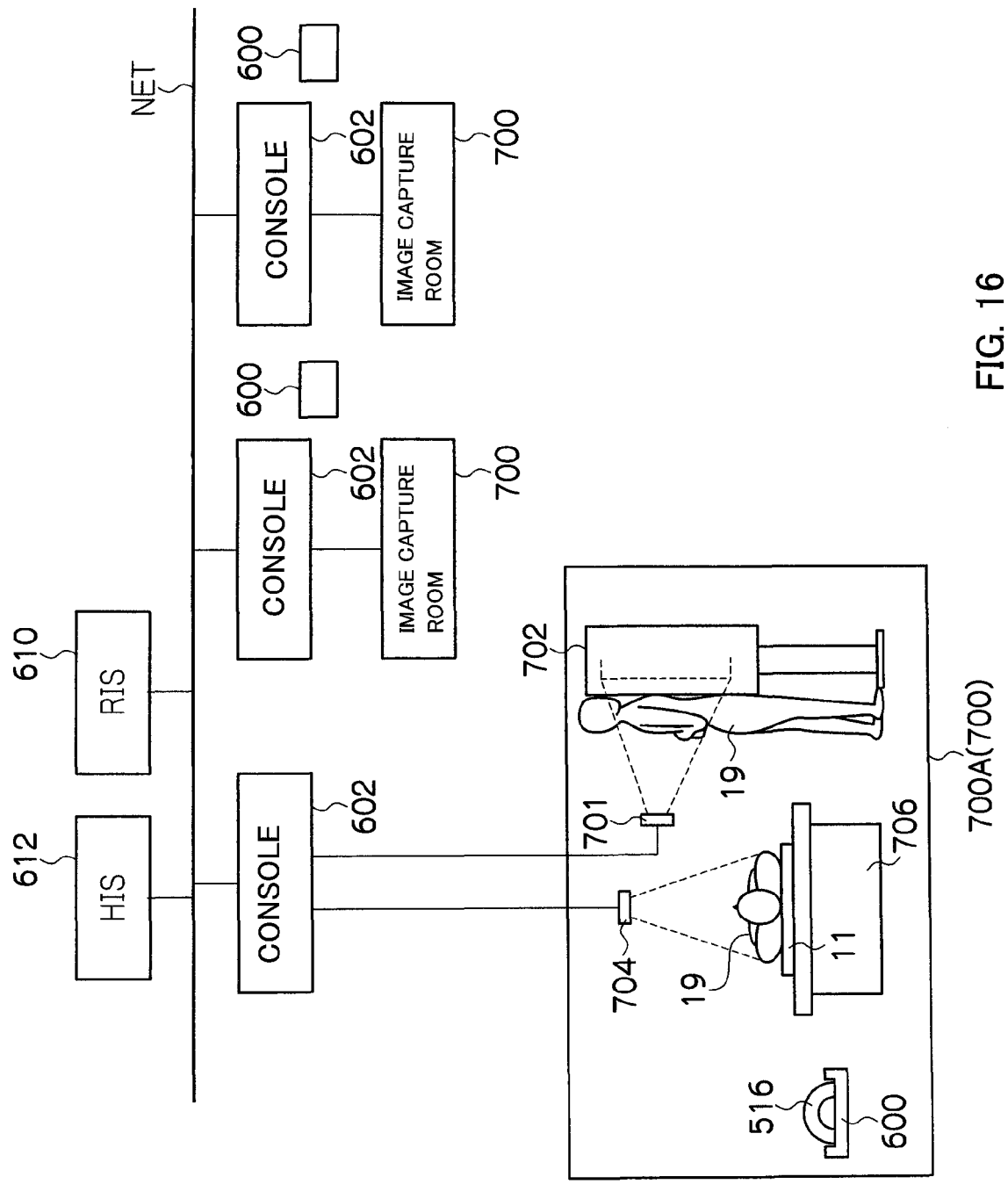
FIG. 16 is a block diagram showing the schematic structure of the radiographic image detection system in a hospital.

As shown in FIG. 16, in each of image capture rooms 700 in which a radiographic image is captured, an image capture device 702 that captures a radiographic image and the console 602 that controls the image capture device 702 is usually provided. The console 602 is connected to Radiology Information System (RIS) 610 and Hospital Information System (HIS) 612 via a hospital network NET including wired or wireless Local Area Network (LAN). By additionally providing the cradle 600 to the console 602, an electronic cassette can be used for image capture in the image capture room 700.

For example, an image capture in lateral position may be possible in the image capture room 700A by providing a radiation generator 704 for image capture in lateral position, and a bed 706 for the subject 19 to lie down, in addition to the image capture device 702 for image capture in upright position, the cradle 600. Further, the image capture device 702 may be provided with a supporting section for supporting the electronic cassette, and when the image capture device 702 is in bad condition, the image capture operation can be substituted by the electronic cassette, which is supported by the supporting section of the image capture device 702.

The cradle 600 may be configured to accommodate plural handles 516 and may set the image capture conditions to the plural handles 516 simultaneously.

As described above, in an aspect of the present invention, the handle portion that is provided so as to be able to be grasped has the notification section that gives notice of the operating state of the radiation detector. Therefore, when the radiographic image detection device is placed in an upright-ing stand or between a bed and a subject, the handle portion that is grasped by the operator is not covered by the subject, and confirmation of the operating state can be carried out easily.

In the radiographic image detection device of the present aspect, the radiation detector may have a mounting portion at which the handle portion can be mounted, and the handle portion is detachable from the mounting portion.

In the present aspect, the mounting portion may be provided at plural positions at the radiation detector.

In the present aspect, the radiation detector may be rectangular; and the mounting portions may be provided respectively at a long-side side surface and at a short-side side surface of the radiation detector.

By making the handle portion detachable from the radiation detector, the portability of the radiographic image detection device improves. Further, in a case in which the radiation detector is rectangular, by providing the mounting portions respectively at a long-side side surface and a short-side side surface, the handle portion can be mounted to a position at which handling is easy in accordance with the orientation of the radiographic image detection device at the time of shooting, and handling is easy.

In the present aspect, the handle portion may include at least one of a power source for driving the radiation detector, and a storage unit that stores the image information output from the radiation detector.

Due to this configuration, the handle may perform at least one of supplying driving power to the radiation detector, or storage of the image information which is detected by the radiation detector. Further, by providing the power source at the handle portion, the radiation detector can be made to be compact.

In the present aspect, the handle portion may include an input section for inputting settings of the radiation detector.

Due thereto, not only confirming of the operating state, but also setting as well can be carried out easily.

In the present aspect, the handle portion may include a communication section for carrying out communication with an external device.

By providing the communication section at the handle portion that is not covered by the subject in this way, it is easy to connect a cable in the case of wired communication, and poor propagation due to the effects of the subject can be prevented in the case of wireless communication.

Another aspect of the invention is a radiographic image detection system including: a radiographic image detection device that includes a radiation detector that detects, based on an image capture condition, radiation that has passed through a subject and has been irradiated thereon, and outputs image information expressing a radiographic image corresponding to a detected radiation amount, and a handle portion provided at a side surface of the radiation detector and configured to be detachable, and having a notification section that gives notice of an operating state of the radiation detector, a power source for driving the radiation detector, and a storage unit that stores image capture condition information that expresses the image capture condition and the image information output from the radiation detector; a handle accommodating device to which the handle is detachable, the handle accommodating device charges the power source of the handle which is accommodated therein and enables access to the storage unit of the handle; and a controller that writes the image capture condition information in the storage unit of the handle which is accommodated in the handle accommodating device, and reads out the image information stored in the storage unit of the handle.

In this configuration, the notification section that gives notice of the operation state of the radiation detector is provided in the handle portion. Since the handle portion is grasped by an operator during positioning of the radiographic image detection device between an upright mount or bed and a subject, the handle portion will not be covered by the subject and, therefore, the operation state of the radiation detector can be easily confirmed.

By configuring the handle portion detachable with respect to the radiation detector, portability of the radiographic image detection device is improved. Further, the handle portion is provided with the power source for driving the radiation detector, and the storage unit that stores the image capture condition information and the image information output from the radiation detector. When the handle portion is accommodated in the handle accommodating device, the power source of the handle portion is charged thereby, and the controller performs to the storage unit of the handle portion writing of the image capture condition information and read-out of the image information. Due to this configuration, there is no need to provide a cable for supplying power or transmitting the image capture condition information to the radiation detector. Moreover, since the image capture preparation can be implemented by attaching the handle portion to the radiation detector, the operation will be simple and easy.

As described above, in accordance with the embodiments of the radiographic image detection device and the radiographic image detection system, confirmation of the operating state can be carried out easily.

What is claimed is:

1. A radiographic image detection device comprising:
a radiation detector that detects radiation that has passed through a subject and has been irradiated thereon, and outputs image data expressing a radiographic image corresponding to a detected radiation amount; and
a handle portion provided at a side surface of the radiation detector and configured to be grasped, and having a notification section that gives notice of an operating state of the radiation detector, wherein
the radiation detector has a mounting portion at which the handle portion can be mounted, and the handle portion is detachable from the mounting portion;
the mounting portion is provided at a plurality of positions at the radiation detector; and
the notice of an operating state of the radiation detector is at least one selected from the group consisting of: a notice of the mounted position of the handle at the time of a previous shooting; a notice that the mounted position of the handle at the time of a current shooting is different from that at the time of a previous shooting; and a notice that image processing for rotating the generated image has been performed based on the mounted position of the handle.

2. The radiographic image detection device of claim 1, wherein:
the radiation detector is rectangular; and
the mounting portions are provided respectively at a long-side side surface and at a short-side side surface of the radiation detector.

3. The radiographic image detection device of claim 1, wherein the handle portion comprises at least one of a power source for driving the radiation detector, and a storage unit that stores the image data output from the radiation detector.

4. The radiographic image detection device of claim 1, wherein the handle portion comprises an input section for inputting settings of the radiation detector.

5. The radiographic image detection device of claim 1, wherein the handle portion comprises a communication section for carrying out communication with an external device.

6. A radiographic image detection system comprising:
a radiographic image detection device according to claim 1, wherein the handle portion further comprises a power source for driving the radiation detector, and a storage unit that stores image capture condition information that expresses the image capture condition and the image data output from the radiation detector;
a handle accommodating device to which the handle portion is detachable, the handle accommodating device charges the power source of the handle portion which is accommodated therein and enables access to the storage unit of the handle portion; and
a controller that writes the image capture condition information in the storage unit of the handle portion which is accommodated in the handle accommodating device, and reads out the image data stored in the storage unit of the handle portion.

* * * * *